United States Patent [19]

Sangenis et al.

[11] 4,035,147

[45] July 12, 1977

[54] CELLULOSIC MATERIALS CAPABLE OF ABSORBING WATER OF AQUEOUS SOLUTIONS, AND THEIR PRODUCTION

[75] Inventors: Solange Sangenis, Grenoble; Gilbert Guiroy, Saint-Egreve, both of France; Jean Quéré, Risjwick, Netherlands

[73] Assignee: Centre Technique de l'Industrie des Papiers, Cartons et Celluloses, Grenoble Cedex, France

[21] Appl. No.: 457,345

[22] Filed: Apr. 2, 1974

[30] Foreign Application Priority Data

Apr. 5, 1973 France .............................. 73.12376

[51] Int. Cl.$^2$ ....................................... D06M 13/14
[52] U.S. Cl. ............................ 8/116.4; 162/157 C
[58] Field of Search ...................................... 8/116.4

[56] References Cited

U.S. PATENT DOCUMENTS

| 3,046,079 | 7/1962 | Reeves et al. | 8/116.4 |
| 3,069,311 | 12/1962 | Harpham et al. | 162/146 |
| 3,224,926 | 12/1965 | Bernardin | 162/146 |
| 3,310,363 | 3/1967 | Russell et al. | 8/116.4 |
| 3,371,983 | 3/1968 | Barber et al. | 8/116.4 |

*Primary Examiner*—Carman J. Seccuro
*Attorney, Agent, or Firm*—Cushman, Darby & Cushman

[57] ABSTRACT

Cellulosic materials having a high capacity for absorption of water or aqueous solutions, a large volume:-weight ratio and a high resilience are produced by an acid-catalyzed cross-linking reaction in a reaction medium of low water content from a cellulosic or lignocellulosic material in the form of individual, substantially dehydrated, non-swollen and inter-fibre-bonds free fibres.

27 Claims, 2 Drawing Figures

Fig.1.
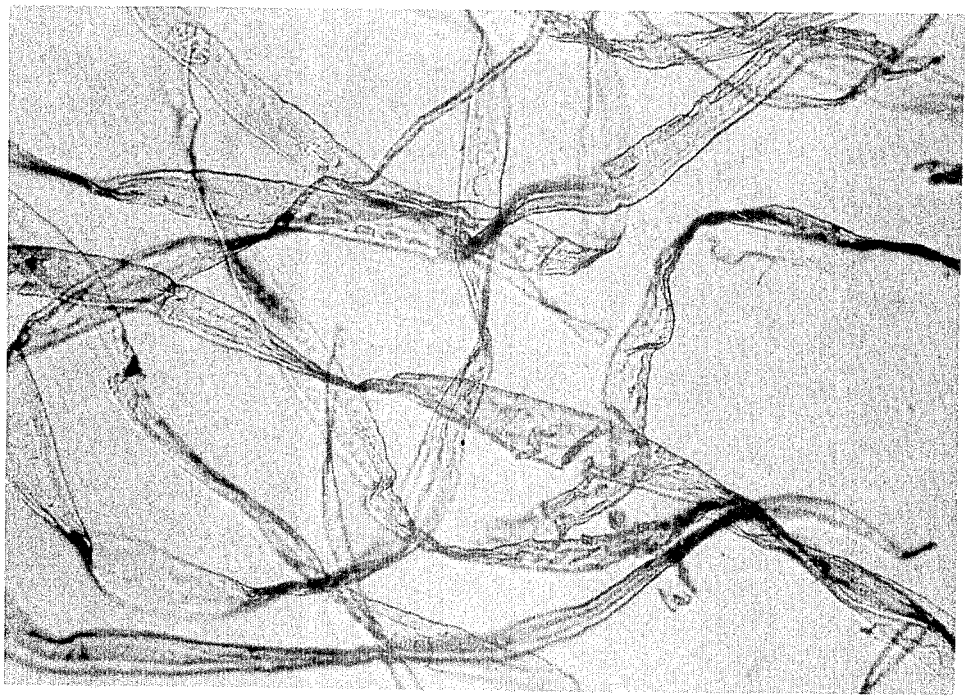
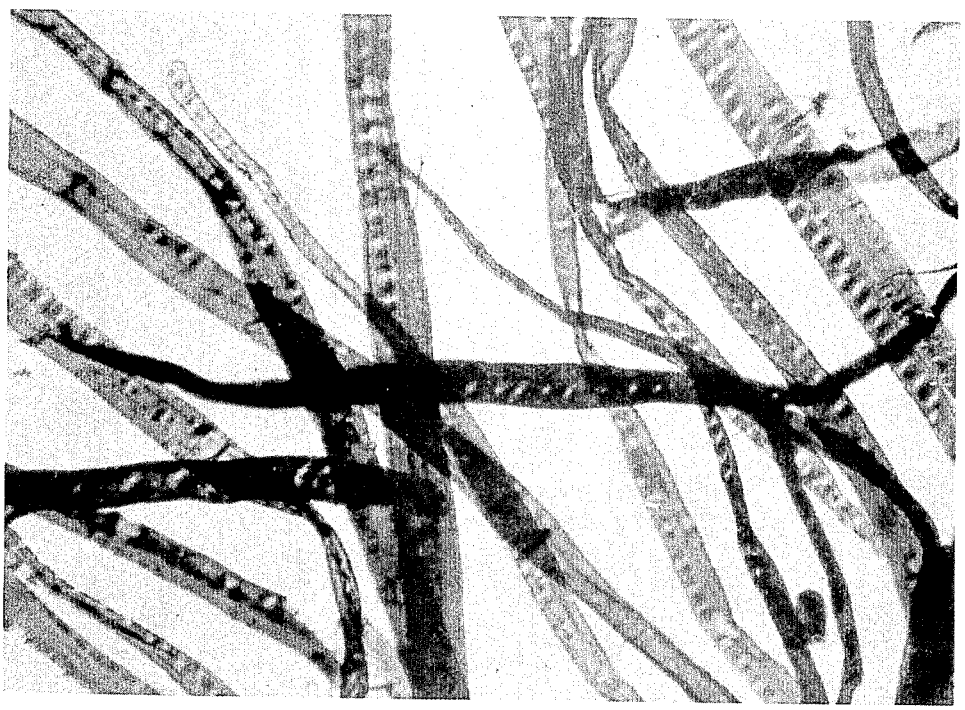
Fig.2.

CELLULOSIC MATERIALS CAPABLE OF ABSORBING WATER OF AQUEOUS SOLUTIONS, AND THEIR PRODUCTION

The invention is concerned with novel materials having substantial capacitites for absorption of water, or more generally, aqueous solutions, together with a large volume: weight ratio, and a high level of resilience.

An ever increasing number of uses is being found for such materials, for example in the non-woven material industry, the uses of which materials tend to multiply. For example, non-woven materials are used on an ever increasing scale, and for the production of sanitary and domestic articles such as disposable diapers or napkins, sanitary towels and tampons, surgical cloths and disposable linen. Non-woven materials are also being increasingly used for example in the field of industrial cleaning or for the production of materials for absorbing aqueous fractions contained in heterogeneous systems with immiscible phases, one of which is aqueous.

Attempts have certainly already been made to use, for such fabrications, cellulosic materials which have a generally fibrous structure, such as wood pulps or cotton linters. The cellulosic fibres of such wood pulps or cotton linters do not normally have substantial absorbent properties as regards to water or aqueous solutions.

In order to overcome this disadvantage, it has already been proposed that sheets should be formed from pulps produced from suspensions of paper-making cellulosic fibres in water, to which surface-active agents had previously been added.

This treatment however does not sufficiently increase the capacity of the resulting fibrous materials to absorb liquids, particularly when the materials must be re-suspended in water and then dried. This applies especially when the desired final products, for example non-woven materials, are produced by "wet processes", which are well known in the paper-making art.

It has also been proposed that the absorptive capacities of the materials produced from cellulosic pulps be improved by subjecting such pulps to a cross-linking operation with bi-functional agents or formaldehyde. In some cases a certain improvement in the absorption properties of the pulps treated in this way is in fact achieved.

U.K. patent specification No. 1,233,109 states in fact that it is possible to produce materials having the appearance of a textile material by subjecting unbeaten cellulosic pulps to a cross-linking treatment with polyfunctional cross-linking agents.

Similarly, French Pat. No. 1,431,177 describes an absorbent product which is produced from cellulosic fibres that have been treated in the wet condition, i.e., when the fibres are in the swollen state, by a cross-linking agent such as formaldehyde within an aqueous bath. According to this French Patent, the absorptive capacity of the products made from cellulosic fibres subjected to cross-linking in the dry state is approximately the same as that of the products made from untreated cellulosic fibres. In other words, cross-linking in the dry condition would hardly improve the defective absorptive properties of untreated celluloses, as regards absorption of water or aqueous solutions.

However, the products resulting from the known cross-linking processes, particularly when applied to cellulosic fibres of paper-related origin, possess neither satisfactory qualities in respect of absorption of liquids nor a volume:weight ratio and a resilience sufficient to permit their efficient use in the technical fields referred to above, even when under the most favorable conditions set out in the prior documents.

It is an object of the present invention to overcome the above disadvantages.

It is a further object of the present invention to provide a process which makes it possible to manufacture, from any cellulosic fibrous materials whatever, products that have a high capacity for absorption in respect to water or aqueous solutions, a particularly large volume: weight ratio, and a particularly high level of resilience.

It is a further object of the present invention to manufacture from paper-making pulps products having a high capacity for absorption of aqueous liquids a low density and a high resilience.

Other objects and advantages of the present invention will follow from the succeeding discussion.

The invention is based on the discovery that the initial physical condition of the fibres subjected to the cross-linking reaction is a particularly important parameter in relation to the qualities desired in the finished material as regards absorption, volume: weight ratio, and resilience. The operation of rendering the fibres individual and drying them represents one of the particularly important contributions of the invention.

In accordance with the present invention, cellulosic (including lignocellulosic) material is treated as follows to produce a product having desirable properties: the cellulosic material to be treated is put into the form of fibres that are substantially non-swollen, dehydrated, rendered substantially individual and devoid of inter-fibre bonds; a cross-linking operation using a cross-linking agent in the presence of an acid catalyst is then carried out on the fibres in a medium in which the water content is sufficiently reduced to avoid swelling of such fibres during cross-linking thereof.

The invention also provides the products themselves as produced by carrying out the novel process.

Preventing the dangers of swelling under the effect of water during the cross-linking operation is also an important aspect of the invention. Failure to remove the inter-fibre bonds which exist in particular in dry pulps and/or to avoid a too high water content in the reaction medium, result in a substantial reduction in the desired characteristics of the final product.

On the other hand, when the above-mentioned conditions are observed, the final products have a high capacity for absorption of liquids by a capillary action, together with a particularly large volume:weight ratio and a particularly high degree of resilience. They are also characterised by a high degree of suppleness and a particular softness to the touch. The fibres of such compositions are substantially antibinding and non-hydratable, particularly by beating. A large number of the fibres have a characteristic curled or cromped and twisted appearance. This appearance is maintained even when the fibres are placed in a swelling medium, for example the Herzberg reagent (zinc chloro-iodide solution).

When the available raw material is a dry paper pulp, it is essential to render the cellulosic fibres individual, more particularly to remove inter-fibre bonds.

This can be effected either by dry shredding, carding, or crushing, taking care not to damage the fibres to an excessive extent. In another embodiment of the method according to the invention, the pulp is dispersed in water, the dispersion is filtered, and the wet fibres are pressed to remove a part of the water, the mass, which is still wet, finally being treated at least once with a completely water-miscible solvent that does not swell cellulose, for example acetone, in order to remove the residual water content in the mass, without creating inter-fibre bonds. This operation is preferably completed by a drying operation, which may involve heating, to produce dry, dehydrated individualized fibres in a non-swollen condition.

It is important in the foregoing, in particular in the course of the above-mentioned pressing operation, to avoid any operation comparable to drying the mass of fibres as opposed to the individualized fibres, insofar as that mass would contain appreciable amounts of water. Drying under such conditions would result in the re-formation of inter-fibre bonds which is precisely what is to be prevented.

Also, when the raw material available comprises a suspension of fibres of the type normally used for producing dry pulps by pressing the suspension until, for instance, a 20 to 30% dry mass (i.e. a mass containing 20 to 30 g. of cellulose per 100 g of the mass) results, and then drying, it is obviously possible to omit the drying operation and to subject the pressed but still moist mass directly to solvent exchange under the conditions set out above.

Also, when the raw material comprises a suspension of fibres, it is obviously possible to dry the pulp and then subject it to a mechanical treatment for rendering the fibres individual, of the nature set out above. This process of individualizing the fibres in two stages, can be more economical in some cases than the process carried out by solvent exchange.

Briefly, the cohesion between the dried and individualized fibres finally produced must be virtually provided only by the interentwinement thereof. The fibres can then be separated from each other without force, in contrast to the fibres of dried pulps which have a relatively high level of cohesion, so that it is not possible for them to be separated in the dry condition without the application of a substantial mechanical force.

The above-described fibre individualization and drying treatment then permits of extremely rapid cross-linking in the presence of a cross-linking agent and an acid catalyst, preferably a halogen acid such as hydrochloric acid, in a medium having as low a water content as possible. It is sufficient to use very small amounts of cross-linking agent to produce a material which is capable of providing, in particular by means of a conventional dry or wet process mats of fibres having a particularly high capacity of water absorption, a particularly large volume:weight ratio and a particularly high level of resilience.

For the cross-linking operation, any of the conventional agents for cross-linking cellulose can be used, for example those listed in U.S. Pat. No. 2,971,815. Among these are glyoxal, tetraoxan, glutaraldehyde, and tetrakis (hydroxymethyl) phosphonium chloride. Particularly good results are obtained with formaldehyde.

Acetone, diosan and acetic acid are examples of solvents used in this process.

The water content of the reaction medium must not normally exceed 20%, and is preferably less than 7%.

Very good results are obtained when the weight of acid catalyst is from 0.02% to 0.9% of the total weight of the reaction medium. Even better results can be obtained with higher proportions of halogen acid, for example up to 5% of the total weight of the reaction medium. This is in no way an upper limit. The upper limit can be limited by considerations of a practical nature. For example, when the acid is introduced into the medium by way of an aqueous solution, the upper limit is linked to the maximum concentration of hydrochloric acid which can be obtained in an aqueous solution, and the amount of the latter than can be added to the medium.

The amount of cross-linking agent, such as formaldehyde, used is not limited towards the upper values. The reaction proceeds rapidly, even when the proportion of formaldehyde in the medium is less than 1% by weight of the medium. This is of advantage from the economic point of view. Particularly good results are obtained when the amounts of halogen acid, in particular hydrochloric acid, and cross-linking agent, in particular formaldehyde, are in an acid/cross-linking agent molar ratio of from 0.5 to 1.5, and advantageously close to 1.

The reaction can be carried out at ambient temperature of at a higher temperature. In particular, operation is advantageously effected at from 15° to 60° C, preferably from 40° to 55° C.

The amount of water introduced into the reaction medium should normally be limited to the amount in the formaldehyde solution used in the reaction. This addition will however be extremely small if consideration is taken of the fact that the reaction can be efficiently carried out with very small proportions of formaldehyde.

In a particular embodiment of the process according to the invention, the individualized and dehydrated fibres are brought into contact with the medium containing all the agents necessary for the cross-linking reaction at ambient temperature and, after a very short time, for example one minute, the fibres are squeezed by centrifuging and the temperature is then raised to a value at which cross-linking proceeds rapidly, preferably at from 40° to 55° C.

The very short contact time mentioned above is sufficient to permit of homogeneous distribution of the cross-linking agent and the acid catalyst in the fibres, and the reaction can then proceed rapidly in the mass of fibres obtained after centrifuging. This manner of proceeding has the advantage that it makes it possible to limit to the maximum extent the amount of reagents effectively involved in the course of the cross-linking operation. It is necessary to heat only the concentrated centrifuge-squeezed mass of fibres to the above-mentioned cross-linking temperature, which economizes on heat and gives the possibility of operating in smaller units.

The liquid fraction recovered in the course of the centrifuge-squeezing operation can be re-used directly, after restoration of its initial content of each of the reagents, to treat a fresh mass of individualized and dehydrated fibres.

The reaction proceeds very rapidly, particularly when the cross-linking operation is carried out at a temperature of from 40° to 55° C. By way of example, the reaction time is usually from 30 seconds to 30 minutes.

The existence of cross-linking in the materials produced from the above-described treatments is demonstrated by the fact that they are insoluble in the conventional solvents for cellulose, such as cadoxene, or cupriethylene-diamine. The amount of cross-linking agent fixed on the cellulose, when the cross-linking agent is formaldehyde, is titrated by the method described by Boyd and Logan (Formaldehyde, Reinhold Publishing Corporation, American Chemical Society Monograph Series, pages 469–470), with chromotopic acid.

The effects of the cross-linking can be appreciated by measuring the water-retention value (referred to hereinafter as WRV), the absorption capacity of sheets produced with the material obtained, and the volume:-weight ratio of such sheets.

The WRV was measured by the method described by AM SCALLAN and J E CARLES (Svensk Papperstidnings Vol 75, No. 17–30th September 1972, pages 699 to 703). The principle of this measuring operation comprises determining the amount of water retained in the fibres under study, after centrifuging. The results given hereinafter in the examples were obtained after centrifuging with a centrifugal force of 900 g for 30 minutes.

The WRV is expressed in grams of water retained per gram of dry pulp centrifuged (g/g). The materials according to the invention have particularly low WRVs.

The water-absorption capacity is measured as follows: the cross-linked material is washed until neutrality, and then dispersed in water. A laboratory machine (Noble-Wood formette) is then used to produce sheets weighing 375 g/sq.m which are squeezed without heating between blotter papers with a roller weighing 500 g. the sheets then being dried at a temperature of from 100° to 105° C. The absorption test is then carried out on half sheets. The sample to be tested is weighed with a high degree of accuracy, placed on a wire stretched in a frame, and immersed for a period of 3 minutes in a water bath at ambient temperature. The assembly is then taken out of the water and placed so that a diagonal of the frame is in a vertical plane and inclined at an angle of 45° with respect to a horizontal plane. The assembly is left to drain for 1 minute, then turned through 180°, and then left to drain for another minute. The assembly is then weighed and the weight of absorbed water is inferred thereof.

The water absorption capacity is also expressed in $g$ of absorbed water by $g$ of dry pulp. It is particularly high in the case of materials according to the invention.

The mats of fibres produced from the fibres treated by the process according to the invention have a very substantial volume:weight ratio. The measurements of volume:weight ratio as given in the following examples, were all carried out under a pressure of 6 millibars, except when another pressure value is specified.

As will appear from the data relating to preferred embodiments below, the process of the present invention can be used to produce individual and totally antibinding fibres, which result in fibrous structures (at least when the initial material treated is fibrous) characterised by a particularly high capacity for absorption of liquids, a particularly large volume: weight ratio, a particularly high level of resilience, a high degree of flexibility and a particularly soft touch.

Some at least of the cross-linked fibres produced by the process according to the invention have a characteristic curled and twisted appearance. FIG. 1 of the accompanying drawing is a reproduction of a micrograph (degree of enlargement 200) of fibres produced in accordance with the invention, after residing for 1 hour in a medium which normally has a swelling action on cellulosic fibres and which comprises a solution known under the name of "Herzberg reagent" (zinc chloro-iodide solution). The fibres involved are those produced under the conditions described in Example 3 for test 8.

This micrograph shows the twisted appearance of the treated fibres. They have suffered virtually no swelling effect under the action of the Herzberg reagent.

The micrograph shown in FIG. 1 is to be compared with that shown in FIG. 2. This shows the appearance of cellulosic fibres of the same origin but that have not been treated in accordance with the process of the invention. Like the fibres in FIG. 1, they remained for 1 hour in the Herzberg reagent. FIG. 2 brings out the swollen and relatively regular appearance of the untreated fibres. The swelling of such fibres can also be appreciated by the amount of iodide which they have absorbed and which turns them a violet colour.

Besides using the materials formed for producing liquid-absorbent materials, particularly in the form of mats, the materials formed can be incorporated in various kinds of fibrous network systems, particularly in non-woven materials, absorbent waddings, highly porous papers for impregnation, and in any fibrous structures for which a low density is desired.

The fibres modified in accordance with the invention impart to the non-woven materials in which they are incorporated a flexibility and softness of touch which it was difficult to achieve hitherto. Generally, the modified fibres according to the invention can be used for forming fibrous mattress members and network systems, which are produced by a dry method or by a wet method, using the known processes.

The materials of the type in question are characterised by a very low pressure drop in filtration, which makes it possible also to envisage their use for example for the maintenance of pipe systems.

EXAMPLE 1

Some bleached kraft pulp from softwood is disintegrated in water in a concentration of 4% of paste in the water. This fibre separation treatment would not be necessary in the case of pulps which have never been dried. After filtering, the pulp is washed with acetone. After a further filtering operation, a cake of fibres containing an acetone-water is produced.

In test 3 below, the wash with acetone is repeated.

Acetone, formaldehyde and hydrochloric acid are then added in varying quantities, depending on the desired final concentrations. The pulp is left in the reaction medium for 6 hours at ambient temperature. The excess of the reagent is then removed by filtering and washing with water until neutrality is attained. In an industrial process, the excesses of reagents can be re-used, after adjustment of the levels of concentration.

The conditions of treatment and the results are given in the following table.

| Reference of the tests | 1 | 2 | 3 | 4 | Control (untreated fibres) |
|---|---|---|---|---|---|
| Number of washings with acetone | 0 | 1 | 2 | 1 | — |
| Composition of the medium % by weight Fibres (on a dry basis) | %4 | 4 | 4 | 4 | — |

-continued

| Reference of the tests | 1 | 2 | 3 | 4 | Control (untreated fibres) |
|---|---|---|---|---|---|
| HCHO | %2 | 2 | 2 | 4 | — |
| HCl | %0.9 | 0.8 | 0.9 | 0.8 | — |
| H$_2$O | %16.8 | 6.8 | 6.5 | 11.3 | — |
| CH$_3$—CO—CH$_3$ | %76.3 | 86.4 | 86.6 | 79.9 | — |
| H CHO combined | %0.4 | 0.9 | 1.1 | 0.7 | — |
| Capacity for absorption of water | g/g 5.4 | 13.4 | 16.7 | 8.9 | 4.3 |

The capacity for absorption of water was measured in accordance with the method described above, on fibrous mats formed by a wet process, using conventional paper-making procedures. Tests 1 to 4 show the very important influence of the concentration of water in the reaction medium. The capacity for absorption of water is markedly higher when dehydration of the pulp before reaction with formaldehyde is taken to a greater degree (Test 3).

EXAMPLE 2

Unbeaten bleached kraft pulp from softwood is treated in accordance with the mode of operation as described in Example 1, except that before the cross-linking treatment the pulp is dehydrated by washing with acetone and then dried, either in the form of a cake in a drying oven at from 100 to 105° C (Test 5) or by passing through a cyclone drier (Test 6). The cross-linking treatment is carried out at a temperature of 20° C for a period of 6 hours.

The other experimental conditions and the results are shown in the following table.

| Reference of the test | 3 | 5 | 6 |
|---|---|---|---|
| Drying after washing with acetone | Nil | Drying oven | Cyclone drier |
| Composition of the reaction medium | | | |
| Fibres (on a dry basis) | % 4 | 4 | 4 |
| HCHO | % 2 | 2 | 2 |
| HCl | %0.9 | 0.9 | 0.9 |
| H$_2$O | %6.5 | 6.0 | 6.2 |
| CH$_3$—CO—CH$_3$ | %86.6 | 87.1 | 86.9 |
| H CHO combined | %1.1 | 1.2 | 1.9 |
| Capacity for absorption of water | g/g 16.7 | 20.2 | 21.4 |

The water absorption capacity of the fibres improves as preliminary dehydration of the fibres is taken to a more advanced degree. The water absorption capacity is markedly improved under the conditions of tests 5 and 6.

EXAMPLE 3

A bleached kraft pulp from softwood is treated in accordance with the mode of operation described in Example 2. Before reaction the pulp is washed with acetone and dried in a cyclone drier. The composition of the reaction medium is identical to that of test 6. The reaction temperature is 50° C instead of 20° C, and the reaction time is varied from 1 minutes to 6 hours. The results are given below.

| Reference of the test | 7 | 8 | 9 | 11 | 12 |
|---|---|---|---|---|---|
| Reaction time in minutes | 1 to 2 | 5 to 6 | 15 | 120 | 360 |
| HCHO combined | % 0.6 | 1.3 | 1.3 | 2 | 2 |
| Capacity for absorption of water g/g | 16.5 | 22.2 | 19.8 | 20.8 | 18.7 |
| volume:weight ratio ccm/g | 11.9 | 31.2 | 30.3 | 24.8 | 22.5 |

It is found that a prolonged treatment does not improve the performance of the materials produced. On the contrary, the performance of the materials would tend to decrease after a given time.

It is found that under these conditions the desired effect is very rapidly achieved. After 5 minutes of reaction, the water absorption capacity and the volume:-weight ratio reach values of 22.2 g/g and 31 ccm/g respectively.

EXAMPLE 4

A bleached kraft pulp from softwood is treated in accordance with the method described in Example 3, but the concentration of formaldehyde is reduced. The conditions of the experiment and the results are given in the following table.

| References of the tests | 13 | 14 | 15 |
|---|---|---|---|
| Composition of the reaction medium | | | |
| Fibres (on a dry basis) | % 4 | 4 | 4 |
| HCHO | % 0.4 | 0.4 | 0.4 |
| HCl | % 0.9 | 0.9 | 0.9 |
| H$_2$O | % 2.63 | 2.63 | 2.63 |
| CH$_3$CO CH$_3$ | % 92.17 | 92.17 | 92.17 |
| Temperature of the reaction | ° C 20 | 50 | 50 |
| Time | Minute 360 | 5 | 1 |
| HCHO combined | % 1.4 | 0.7 | 0.6 |
| Capacity for absorption of water | g/g 22 | 21.5 | 17.2 |
| volume:weight ratio | ccm/g 22.6 | 17 | 11.4 |

The tests of this Example show that it is possible to substantially reduce the amount of formaldehyde without impairing the efficiency of the treatment as regards the capacity for absorption of water.

EXAMPLE 5

A bleached kraft pulp from softwood is cross-linked under conditions similar to those of test 14 of Example 4, except that the concentration of the acid catalyst is varied. The experimental conditions and the results appear in the following table. The temperature is 50° C and the reaction time is 5 minutes.

| Reference of the tests | 14 | 16 | 17 | 18 | Control (untreated pulp) |
|---|---|---|---|---|---|
| Composition of the reaction medium | | | | | |
| Dry fibres | % 4 | 4 | 4 | 4 | |
| HCHO | % 0.4 | 0.4 | 0.4 | 0.4 | |
| HCl | % 0.9 | 0.4 | 0.2 | 0.02 | |
| H$_2$O | % 2.63 | 1.78 | 1.49 | 1.25 | |
| CH$_3$COCH$_3$ | % 92.17 | 93.42 | 93.81 | 93.33 | |
| HCHO combined | % 0.7 | 0.74 | 0.65 | 0.56 | Nil |
| WRV | g/g 0.48 | 0.68 | 0.72 | 0.85 | 1.24 |
| Water absorption capacity volume: | g/g 21.5 | 18 | 16.4 | 12 | 4.3 |

-continued

| Reference of the tests | | 14 | 16 | 17 | 18 | Control (untreated pulp) |
|---|---|---|---|---|---|---|
| weight ratio | ccm/g | 17 | 18.5 | 13.7 | 10.1 | 3.9 |

The capacity for absorption of water and the volume:weight ratio decrease when the concentration of acid catalyst is reduced. However, even with a very low HCl concentration (0.02%), these characteristics reach a level which is greatly higher than that of the untreated pulp. In addition, the WRV was measured, the value thereof depending on the degree of cross-linking. It is surprisingly found that a high water absorption capacity and a large volume:weight ratio correspond to a low WRV. This group of characteristics is particularly advantageous for uses in the field of non-woven fabrics. Incorporating the cross-linked fibres in non-woven materials makes it possible to attain qualities of flexibility and softness of touch, and in the field of filtering pads and other mats, a low resistance to filtration, as the fibres do not swell.

EXAMPLE 6

A bleached kraft pulp from softwood is cross-linked under conditions similar to those of test 9 of Example 3, except for the concentration of acid catalyst which is higher in this test (test 28). The experimental conditions and the results appear in the following table.

Test 28 shows that the increase in the proportion of acid with respect to that of the formaldehyde (the other parameters of test 28 being fairly close to those of test 9) results in a considerable increase both in the water absorption capacity and in the volume:weight ratio of the products obtained.

| Reference of the tests | | | 9 | 28 |
|---|---|---|---|---|
| Composition of the reaction medium: | | | | |
| Fibres (on a dry basis) | | % | 4 | 4 |
| HCHO | | % | 2 | 1.8 |
| HCl | | % | 0.9 | 2.2 |
| $H_2O$ | | % | 6.2 | 8.2 |
| $CH_3COCH_3$ | | % | 86.9 | 83.8 |
| Reaction temperature | | °C | 50 | 50 |
| Time | | min | 15 | 15 |
| HCHO combined | | % | 1.3 | 1.5 |
| Water absorption capacity | | g/g | 19.8 | 31.4 |
| Volume:weight ratio (at 1 millibar) | | ccm/g | 30.3 | 50.7 |
| WRV | | g/g | — | 0.36 |

Following examples 7 to 10 show that the process can be applied to different kinds of pulps (chemical, semi-chemical, mechanical, bleached or unbleached, beaten or unbeaten pastes).

The results obtained in each case are given in the corresponding tables.

EXAMPLE 7

A bleached sulphite pulp from softwood is treated in accordance with the mode of operation described in Example 2. The proportions of the reagents are the same as those in test 6 of Example 2. The following are obtained:

| Reference of the tests | | 19 | 20 | 21 |
|---|---|---|---|---|
| Temperature | °C | 20 | 50 | 50 |
| Time | | 6 hrs | 5 mins | 15 mins |

-continued

| Reference of the tests | | 19 | 20 | 21 |
|---|---|---|---|---|
| Water absorption capacity | g/g | 19.4 | 17.6 | 20.4 |
| Volume:weight ratio | ccm/g | 16.8 | 20.4 | 20.8 |
| HCHO combined | % | 1 | 1.07 | 1.5 |

EXAMPLE 8

A flash-dried mechanical pulp is treated like the pulp of Example 3 (test 11), except that the reaction is carried out in a period of 5 minutes at a temperature of 50° C.

| Reference of the tests | 22 | Control |
|---|---|---|
| Water absorption capacity | 10 g/g | 3.2 g/g |

EXAMPLE 9

The mechanical pulp of Example 8 is replaced by an unbleached and unbeaten kraft pulp.

| Reference of tests | | 23 | 24 | Control |
|---|---|---|---|---|
| Reaction time | min | 5 | 30 | |
| Water absorption capacity | g/g | 13.8 | 20.5 | 5.7 |

EXAMPLE 10

A bleached kraft pulp from softwood is beaten to 34° SR (Schopper Riegler degrees), and then treated in accordance with the process of the present invention:

| Reference of the tests | | 25 | 26 | Control |
|---|---|---|---|---|
| Drying | | Cyclone | Nil | |
| Reaction time | min | 5 | 5 | — |
| Water absorption capacity | g/g | 18 | 9.7 | 2.5 |
| Volume:weight ratio | ccm/g | 12.4 | 6.3 | 3.6 |
| HCHO combined | % | 0.9 | 0.7 | — |

EXAMPLE 11

This example aims to show that carrying out the reaction in two phases, comprising briefly contacting the dry fibres with the various reactants at ambient temperature, then carrying out the cross-linking operation at a temperature which is a little higher, after previous squeezing the mass, gives results which are substantially equivalent to those obtained without squeezing.

In the following table the results of test 28 of Example 6 (cross-linking but without previous squeezing are repeated.

In test 29, the fibres are contacted with the same amounts of reagent as in test 28. After a contact time of 1 minute, the mass is subjected to an operation of squeezing. Cross-linking is then effected at a temperature which is a little higher (50° C) for a period of 30 minutes.

The table also gives the results of two other tests (tests 30 and 31) which are carried out under substantially similar conditions.

The upper part of the table includes the percentages by weight of each of the components of the reaction medium initially contacted. The central part of the table gives the proportions by weight of the fibres after the preliminary squeezing operation for tests 29, 30 and 31, and likewise the cross-linking times and temperatures, the cross-linking operation obviously having been effected after the squeezing operation in Examples 29, 30 and 31.

The lower part of the table shows the results obtained. Study of these results will show that the results obtained in every case are approximately similar.

| Reference of the tests | | 28 | 29 | 30 | 31 |
|---|---|---|---|---|---|
| Composition of the reaction medium | | | | | |
| Dry fibres | % | 4 | 4 | 7 | 7 |
| HCHO | % | 1.8 | 1.8 | 1.8 | 3.6 |
| HCl | % | 2.2 | 2.2 | 2.2 | 4.4 |
| H$_2$O | % | 8.2 | 8.2 | 8.4 | 16.3 |
| CH$_3$COCH$_3$ | % | 83.8 | 83.8 | 80.6 | 66.7 |
| Concentration of fibres After the squeezing operation | % | No squeezing operation | 16.9 | 60.1 | 57.4 |
| Cross-linking temperature | ° C | 50 | 50 | 50 | 50 |
| Cross-linking time | min | 15 | 30 | 30 | 30 |
| HCHO combined | % | 1.5 | 1.4 | 1.1 | 1.6 |
| Water absorption capacity | g/g | 31.4 | 28.1 | 28.9 | 30.4 |
| Volume:weight ratio (at 1 millibar) | ccm/g | 50.7 | 45.4 | 50.5 | 50.9 |
| WRV | g/g | 0.36 | 0.37 | 0.37 | 0.38 |

EXAMPLE 12

The aim of this example is to provide a comparison between the characteristics of a mat of cross-linked fibres produced by carrying out the process of the invention, and those of the material obtained from an identical cellulosic pulp, in the absence of any preliminary treatment for rendering the fibres individual, and any particular precautions concerning the water content of the medium in which the cross-linking operation is carried out. The latter material was in particular produced under the following conditions (test 27).

The cellulose pulp was moistened with five fold weight of a solution containing 10 parts of a 35% formaldehyde solution, 10 parts of a 37% hydrochloric acid solution, and 8 parts of water. The fibre suspension produced is left at rest for 5 hours in a closed container, at ambient temperature. The pulp was then filtered and washed until it no longer contained any acid. This paste was used to form, by a wet method, a sheet whose characteristics are given in the following table. The same table also includes, by way of comparison, the results obtained in test 14 of Example 4 above.

| Reference of the tests | | 14 | 27 |
|---|---|---|---|
| Reaction time | min | 5 | 300 |
| HCHO | % | 0.7 | 1 |
| Water absorption capacity | g/g | 21.5 | 12.9 |
| Volume:weight ratio | ccm/g | 17 | 5.9 |

This table shows the very high level of efficiency of the process according to the invention. The invention provides for the production, after reaction for 5 minutes with formaldehyde, of a product having a water absorption capacity which is twice as high, and a volume:weight ratio which is three times as great, as those of the product obtained by carrying out the conventional process over a period of 5 hours.

It will also be noted that in the example of carrying out the known process, it was not possible to observe any cross-linking in the fibres of a specimen taken from the above-mentioned suspension, 5 minutes after wetting the pulp with the above-mentioned solution.

We claim:

1. In a method of treating cellulosic materials by cross-linking said materials with a cross-linking agent in the presence of an acid catalyst, the improvement that comprises putting the cellulosic material to be treated with the cross-linking agent and acid catalyst into the form of dry, substantially dehydrated, non-swollen individualized fibers devoid of inter-fiber bonds, the inter-fiber bonds, if present initially, being broken, and contacting said material in said form, with a medium containing said cross-linking agent and said acid catalyst, the water content of said medium being sufficiently reduced to avoid swelling of the fibers during cross-linking thereof.

2. An improvement according to claim 1 in which the cellulosic material to be treated comprises a papermaking pulp and the pulp in the dry state is subjected, before the cross-linking operation, to a mechanical treatment for separating its fibres by carding, crushing or the like.

3. An improvement according to claim 1, in which the cellulosic material to be treated comprises a wet mass of paper-making cellulosic fibres that are not linked together by inter-fibre bonds, and the mass is subjected to at least one solvent-exchange treatment with a water-miscible solvent capable of extracting water from the fibres.

4. An improvement according to claim 3, in which the fibres, after solvent-exchange treatment, are subjected to a supplementary drying treatment to cause evaporation of the solvent.

5. An improvement according to claim 1, in which the cross-linking agent comprises formaldehyde or an agent capable of liberating formaldehyde in the medium.

6. An improvement according to claim 5, in which the amount of formaldehyde used is 0.4 to 4% by weight of the reaction medium.

7. An improvement according to claim 1, in which the cross-linking reaction is carried out within a medium containing a water-miscible solvent, the water content of said medium being less than 20% of the weight of said medium.

8. An improvement according to claim 7, in which the water content of the reaction medium is less than 7% of the weight of said medium.

9. An improvement according to claim 7, in which the water-miscible solvent comprises acetone, dioxan or acetic acid.

10. An improvement according to claim 7, in which the acid catalyst is a halogen acid and that the amount thereof which is used is from approximately 0.02 to 5% by weight of the reaction medium.

11. An improvement according to claim 10, in which the amount of acid used is from 0.02 to 0.9% by weight of the reaction medium.

12. An improvement according to claim 1, in which the amounts of acid catalyst and cross-linking agent used are in an acid/cross-linking agent molar ratio of from 0.5 to 1.5.

13. An improvement according to claim 8, in which the acid catalyst is hydrochloric acid and the cross-linking agent is formaldehyde and they are used in an acid/formaldehyde molar ratio of from 0.5 to 1.5.

14. An improvement according to claim 12, in which the acid catalyst is hydrochloric acid and the cross-linking agent is formaldehyde.

15. An improvement according to claim 1, in which the reaction is carried out at a temperature of from 15 to 60° C, which temperature is maintained for a period of from 30 seconds to 30 minutes.

16. An improvement according to claim 15, in which the temperature is from 40° to 55° C.

17. An improvement according to claim 1, in which the substantially individualised and dehydrated fibres are contacted at the desired temperature with the medium containing the cross-linking agent and the acid catalyst, for a period sufficient to permit uniform distribution thereof in the fibres, the mass is squeezed, and the temperature is increased to a value that provides for relatively rapid cross-linking of the fibres.

18. An improvement according to claim 17, in which the contacting time at ambient temperature is about a minute, and that the cross-linking temperature is from 40° to 55° C.

19. A method according to claim 1, wherein said cross-linking reaction is carried out at a temperature of from 15° to 60° C.

20. A method according to claim 1, wherein said cross-linking reaction is carried out at a temperature of from 40° to 55° C.

21. A method according to claim 1, wherein the cellulosic material originates from wood pulpes.

22. A method according to claim 1, wherein the cellulosic material originates from cotton linters.

23. A method of treating a cellulosic material which comprises subjecting said material being in the form of a wet mass of individualized cellulosic fibers substantially free of inter-fiber bonds to at least one solvent-exchange treatment with a water-miscible solvent capable of extracting water from the fibers without swelling thereof until the fibers are sufficiently dehydrated to substantially exclude the formation of inter-fiber bonds upon subsequent drying, removing the solvent to obtain fibers devoid of interfiber bonds and in a substantially individualized, debydrated and non-swollen state, contacting said fibers in such state with a liquid medium containing such cross-linking agent and said acid catalyst and having a water content sufficiently reduced to avoid swelling of said fibers during the subsequent cross-linking reaction of said cellulosic material in contact with said medium.

24. A method according to claim 23, wherein said cross-linking reaction is carried out at a temperature of from 15° to 60° C.

25. A method according to claim 23, wherein said cross-linking reaction is carried out at a temperature of from 40° to 55° C.

26. A method according to claim 24, wherein the water content of the reaction medium, which comprises said cellulosic material and said liquid medium, is less than 20%.

27. A method according to claim 26, wherein said water content is less than 7%.

* * * * *